US00PP32399P2

(12) United States Plant Patent
Mathey

(10) Patent No.: US PP32,399 P2
(45) Date of Patent: Oct. 27, 2020

(54) ***BUDDLEIA* PLANT NAMED 'SMNBDD'**

(50) Latin Name: *Buddleia hybrida*
Varietal Denomination: SMNBDD

(71) Applicant: Megan M. Mathey, Holland, MI (US)

(72) Inventor: Megan M. Mathey, Holland, MI (US)

(73) Assignee: Spring Meadow Nursery Inc., Grand Haven, MI (US)

( * ) Notice: Subject to any disclaimer, the term of this patent is extended or adjusted under 35 U.S.C. 154(b) by 0 days.

(21) Appl. No.: 16/602,667

(22) Filed: Nov. 18, 2019

(51) Int. Cl.
*A01H 5/02* (2018.01)
*A01H 6/00* (2018.01)

(52) U.S. Cl.
USPC ..... Plt./242

(58) Field of Classification Search
USPC ..... Plt./242
See application file for complete search history.

*Primary Examiner* — Susan McCormick Ewoldt
(74) *Attorney, Agent, or Firm* — C. A. Whealy

(57) ABSTRACT

A new and distinct cultivar of *Buddleia* plant named 'SMNBDD', characterized by its compact, upright and outwardly spreading plant habit; freely branching habit; dense and bushy appearance; leathery and durable leaves; freely flowering habit; large and dense conical inflorescences with numerous dark red purple-colored flowers; and good garden performance.

2 Drawing Sheets

Figure 1:
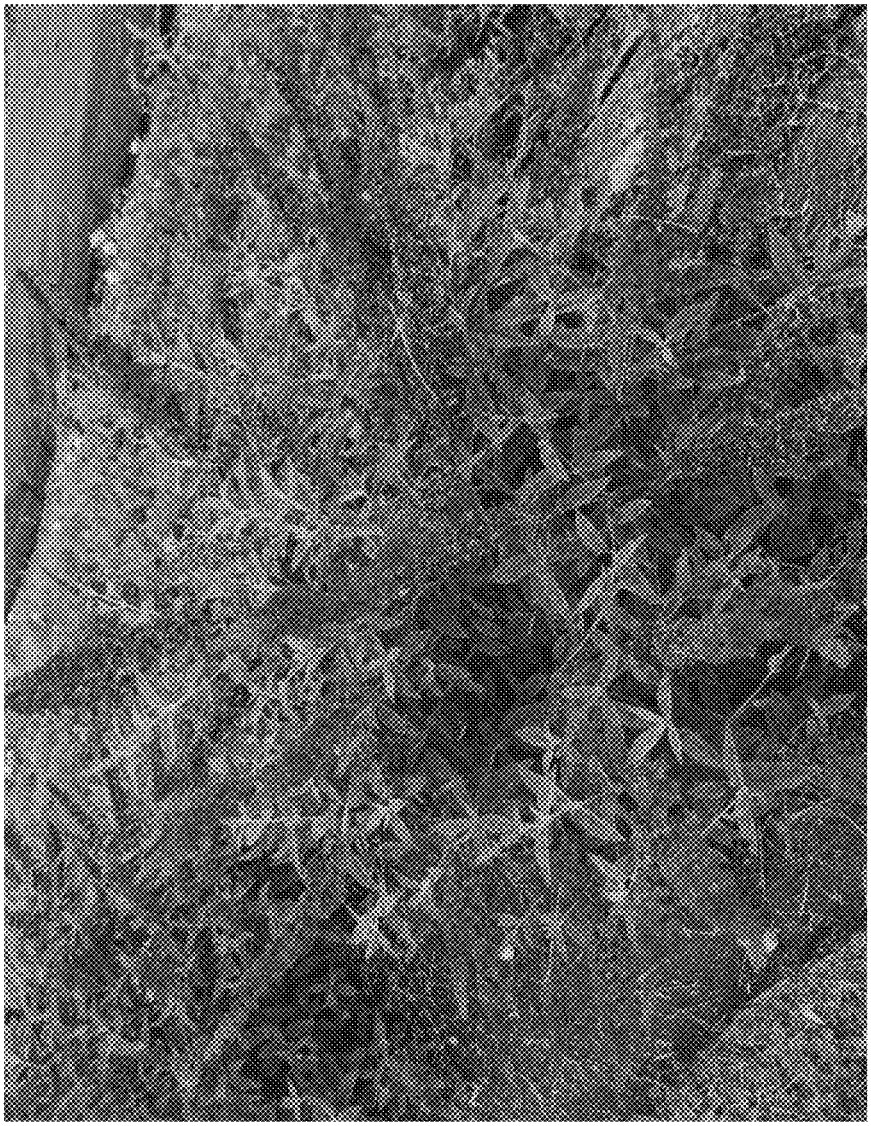

Botanical designation: *Buddleia hybrida.*
Cultivar denomination: 'SMNBDD'.

BACKGROUND OF THE INVENTION

The present invention relates to a new and distinct *Buddleia* plant, botanically known as *Buddleia hybrida* and hereinafter referred to by the name 'SMNBDD'.

The new *Buddleia* plant is a product of a planned breeding program conducted by the Inventor in Grand Haven, Mich. The objective of the breeding program was to create new *Buddleia* plants with strong branches and attractive plant form and flower coloration.

The new *Buddleia* plant originated from a cross-pollination conducted by the Inventor in July, 2015 in Grand Haven, Mich. of *Buddleia hybrida* 'Lilac Chip', disclosed in U.S. Plant Pat. No. 24,016, as the female, or seed, parent with *Buddleia hybrida* 'Miss Molly', disclosed in U.S. Plant Pat. No. 23,425, as the male, or pollen, parent. The new *Buddleia* plant was discovered and selected by the Inventor as a single flowering plant within the progeny of the stated cross-pollination in a controlled environment in Grand Haven, Mich. during the summer of 2017.

Asexual reproduction of the new *Buddleia* plant by softwood stem cuttings in a controlled environment in Grand Haven, Mich. since the summer of 2017 has shown that the unique features of this new *Buddleia* plant are stable and reproduced true to type in successive generations.

SUMMARY OF THE INVENTION

Plants of the new *Buddleia* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'SMNBDD'. These characteristics in combination distinguish 'SMNBDD' as a new and distinct *Buddleia* plant:

1. Compact, upright and outwardly spreading plant habit.
2. Freely branching habit; dense and bushy appearance.
3. Leathery and durable leaves.
4. Freely flowering habit.
5. Large and dense conical inflorescences with numerous dark red purple-colored flowers.
6. Good garden performance.

Plants of the new *Buddleia* differ primarily from plants of the female parent, 'Lilac Chip', in flower color as plants of the *Buddleia* have dark red purple-colored flowers whereas plants of 'Lilac Chip' have purple pink-colored flowers. In addition, plants of the new *Buddleia* have longer inflorescences than plants of 'Lilac Chip'.

Plants of the new *Buddleia* differ primarily from plants of the male parent, 'Miss Molly', in growth habit as plants of the new *Buddleia* are more compact than plants of 'Miss Molly'.

Plants of the new *Buddleia* can also be compared to plants of *Buddleia hybrida* 'Pink Micro Chip', disclosed in U.S. Plant Pat. No. 26,547. In side-by-side comparisons, plants of the new *Buddleia* differ primarily from plants of 'Pink Micro Chip' in the following characteristics:

1. Plants of the new *Buddleia* are larger than plants of 'Pink Micro Chip'.
2. Plants of the new *Buddleia* have larger flowers than plants of 'Pink Micro Chip'.
3. Plants of the new *Buddleia* and 'Pink Micro Chip' differ in flower color as plants of the new *Buddleia* have darker red purple-colored than plants of 'Pink Micro Chip'.

BRIEF DESCRIPTION OF THE PHOTOGRAPHS

The accompanying colored photographs illustrate the overall appearance of the new *Buddleia* plant showing the colors as true as it is reasonably possible to obtain in colored reproductions of this type. Colors in the photographs may differ slightly from the color values cited in the detailed botanical description which accurately describe the colors of the new *Buddleia* plant.

The photograph on the first sheet (FIG. 1 of 2) is a top perspective view of a typical flowering plant of 'SMNBDD' grown in an outdoor nursery.

Figure 2:
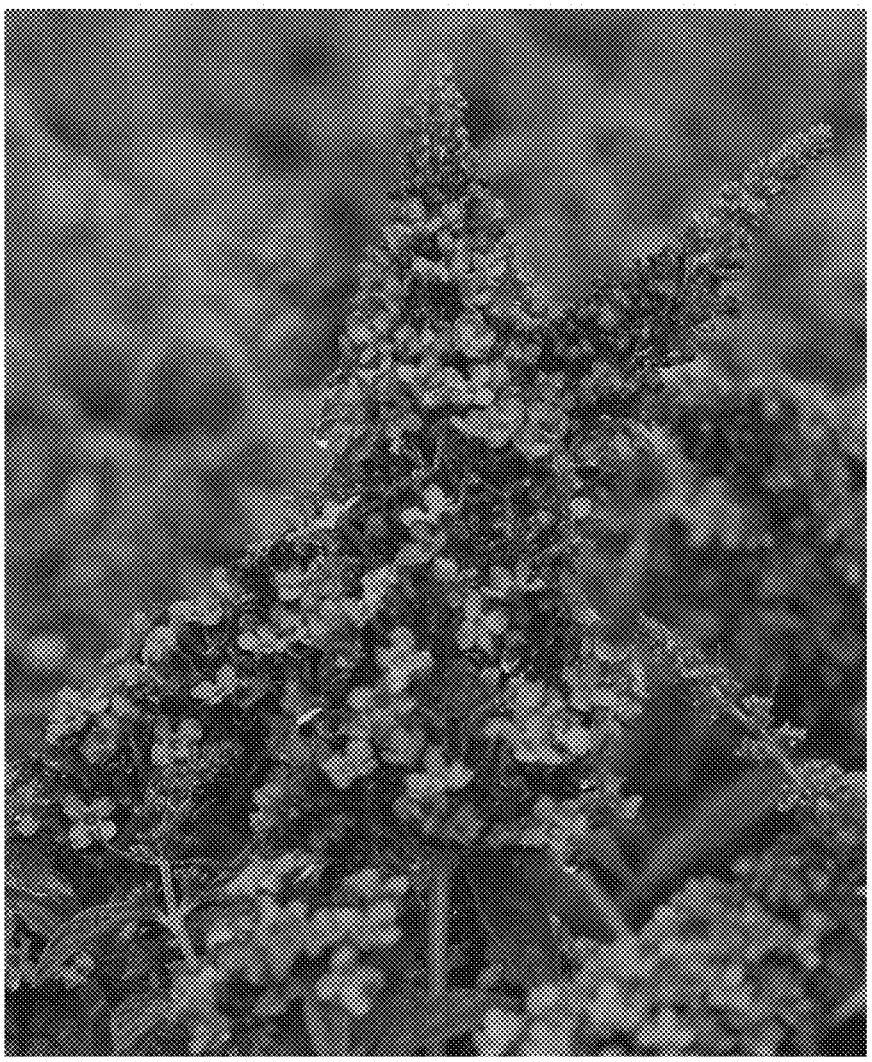

The photograph on the second sheet (FIG. 2 of 2) is a close-up view of typical inflorescences of a plant of 'SMNBDD'.

DETAILED BOTANICAL DESCRIPTION

The aforementioned photographs and following observations, measurements and values describe plants grown during the summer in three-gallon containers in polyethylene-covered greenhouses in Grand Haven, Mich. and under cultural practices typical of commercial production. Plants were two years old when the photographs and description were taken. During the production of the plants, day temperatures ranged from 18° C. to 27° C. and night temperatures ranged from 5° C. to 10° C. In the following description, color references are made to The Royal Horticultural Society Colour Chart, 2015 Edition, except where general terms of ordinary dictionary significance are used.

Botanical classification: *Buddleia hybrida* 'SMNBDD'.

Parentage:

- *Female, or seed, parent.*—*Buddleia hybrida* 'Lilac Chip', disclosed in U.S. Plant Pat. No. 24,016.
- *Male, or pollen, parent.*—*Buddleia hybrida* 'Miss Molly', disclosed in U.S. Plant Pat. No. 23,425.

Propagation:

- *Type.*—By softwood stem cuttings.
- *Time to initiate roots plant, summer.*—About two weeks at temperatures averaging 25° C.
- *Time to produce a rooted plant, summer.*—About 40 days at temperatures averaging 25° C.
- *Root description.*—Fine, fibrous; typically tan in color, actual color of the roots is dependent on substrate composition, water quality, fertilizer, substrate temperature and physiological age of roots.
- *Rooting habit.*—Freely branching; dense.

Plant description:

- *Plant and growth habit.*—Deciduous perennial shrub; compact, upright and outwardly spreading plant habit; rounded appearance; relatively short internodes; dense and bushy appearance; vigorous growth habit.
- *Plant height.*—About 64 cm.
- *Plant width (spread).*—About 80 cm.
- *Lateral branches.*—Quantity: Freely branching habit with about 25 primary lateral branches developing per plant. Length: About 42 cm. Diameter: About 5 mm. Internode length: About 2 cm to 4 cm. Strength: Strong. Aspect: About 15° to 65° from vertical. Texture: Initially, pubescent, then becoming glabrous with development. Color: Close to 199A; pubescence, close to 196A.

Leaf description:

- *Arrangement and appearance.*—Opposite, simple.
- *Length.*—About 8 cm.
- *Width.*—About 3.5 cm.
- *Shape.*—Lanceolate.
- *Apex.*—Acute to acuminate.
- *Base.*—Cuneate.
- *Margin.*—Serrate; slightly undulate.
- *Texture, upper surface.*—Smooth, glabrous, coriaceous.
- *Texture, lower surface.*—Pubescence along midvein, venation prominent; coriaceous.
- *Venation pattern.*—Pinnate.
- *Color.*—Developing and fully expanded leaves, upper surface: Close to NN137A; venation, close to 145C. Developing and fully expanded leaves, lower surface: Close to 148C; venation, close to 138C.
- *Petioles.*—Length: About 6 mm. Diameter: About 2 mm. Texture, upper and lower surfaces: Smooth, glabrous. Color, upper surface: Close to 138A. Color, lower surface: Close to 138C.

Flower description:

- *Flower type and flowering habit.*—Single salverform flowers arranged on terminal and axillary panicles; inflorescences face mostly outwardly; panicles long and conical in shape; freely flowering habit with more than 100 flowers developing per inflorescence; flowers face upright to outwardly depending on position on the panicle; flowers persistent.
- *Fragrance.*—Fragrant; sweet, honey-like, pleasant.
- *Natural flowering season.*—Long flowering period, plants flower continuously from mid-summer into the early autumn in Michigan.
- *Flower buds.*—Height: About 1.5 cm. Diameter: About 1 mm. Shape: Lanceolate. Color: Close to 71A.
- *Inflorescence length.*—About 4 cm to 10 cm.
- *Inflorescence diameter.*—About 2 cm to 3 cm.
- *Flower diameter.*—About 5 mm.
- *Petals.*—Quantity per flower: Typically four in a single whorl. Length: About 3 mm. Width: About 3 mm. Shape: Oblong to obovate. Apex: Obtuse. Base: Slightly acute. Margin: Entire; slightly undulate. Texture, upper and lower surfaces: Smooth, glabrous; soft. Color: Developing petals, upper and lower surfaces: Close to 72A. Fully developed petals, upper and lower surfaces: Close to 72A; color may fade slightly with development.
- *Sepals.*—Quantity per flower: Typically four in a single whorl. Length: About 2 mm. Width: About 0.5 mm. Shape: Lanceolate to ovate. Apex: Acute. Base: Cuneate. Margin: Entire. Texture, upper and lower surfaces: Slightly pubescent. Color, upper surface: Towards the base, close to 145C and towards the apex, close to 143A. Color, lower surface: Close to 145B.
- *Peduncles.*—Length: About 7 mm. Diameter: About 1 mm. Strength: Strong. Angle: Upright to outwardly. Texture: Pubescent. Color: Close to 145B.
- *Pedicels.*—Length: About 1 mm. Diameter: Less than 1 mm. Strength: Strong. Texture: Smooth, glabrous. Color: Close to 145B.
- *Reproductive organs.*—Stamens: Quantity per flower: Typically four. Filament length: About 0.5 mm. Filament color: Close to 26A. Anther length: About 1 mm. Anther shape: Oblong. Anther color: Close to 155B. Pollen amount: Scarce. Pollen color: Close to 11C. Pistils: Quantity per flower: One. Pistil length: About 1 mm. Stigma shape: Oblong. Stigma color: Close to 144B.

*Seeds and fruits*.—To date, seed and fruit development have not been observed on plants of the new *Buddleia*.

Disease & pest resistance: To date, plants of the new *Buddleia* have not been observed to be resistant to pathogens and pests common to *Buddleia* plants.

Garden performance: Plants of the new *Buddleia* have been observed to have good garden performance and tolerate rain, wind and to tolerate temperatures ranging from about −31° C. to about 38° C.

It is claimed:

1. A new and distinct *Buddleia* plant named 'SMNBDD' as illustrated and described.

* * * * *